United States Patent [19]

Svendsen

[11] 4,190,574

[45] Feb. 26, 1980

[54] SUBSTRATE FOR THE QUANTITATIVE DETERMINATION OF PLASMINOGEN ACTIVATORS

[75] Inventor: Lars G. Svendsen, Reinach, Switzerland

[73] Assignee: Pentapharm A.G., Basel, Switzerland

[21] Appl. No.: 798,426

[22] Filed: May 19, 1977

[30] Foreign Application Priority Data

May 28, 1976 [CH] Switzerland .................. 006816/76

[51] Int. Cl.² ...................... C07C 103/52; C12K 1/04
[52] U.S. Cl. ............................... 260/112.5 R; 435/13
[58] Field of Search ............................ 260/112.5 R; 195/103.5 R

[56] References Cited

U.S. PATENT DOCUMENTS

| | | | |
|---|---|---|---|
| 3,884,896 | 5/1975 | Blomback et al. | 260/112.5 R |
| 3,886,136 | 5/1975 | Claeson et al. | 260/112.5 R |
| 4,016,042 | 4/1977 | Svendsen | 260/112.5 R |
| 4,028,318 | 6/1977 | Aurell et al. | 260/112.5 R |
| 4,061,625 | 12/1977 | Af Ekenstam et al. | 260/112.5 R |
| 4,070,245 | 1/1978 | Svendsen | 260/112.5 R |

*Primary Examiner*—Delbert R. Phillips
*Attorney, Agent, or Firm*—Pennie & Edmonds

[57] ABSTRACT

A substrate for the quantitative determination of enzymes in human and mammal body fluids and tissue extracts, which has the structure

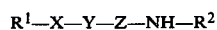

wherein X represents a group having the formula

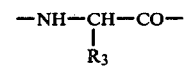

in which $R^3$ is a straight or branched alkyl radical having 1 to 7 carbon atoms or a cyclohexyl or cyclohexylmethyl radical, Y represents a seryl group or a group having the formula $-NH-(CH_2)_n-CO-$ in which n is an integer from 1 to 7, Z represents an arginyl or lysyl group, $R^1$ represents hydrogen or an acyl or sulfonyl group and $R^2$ represents an aromatic hydrocarbon radical which optinally may carry substituents.

5 Claims, 1 Drawing Figure

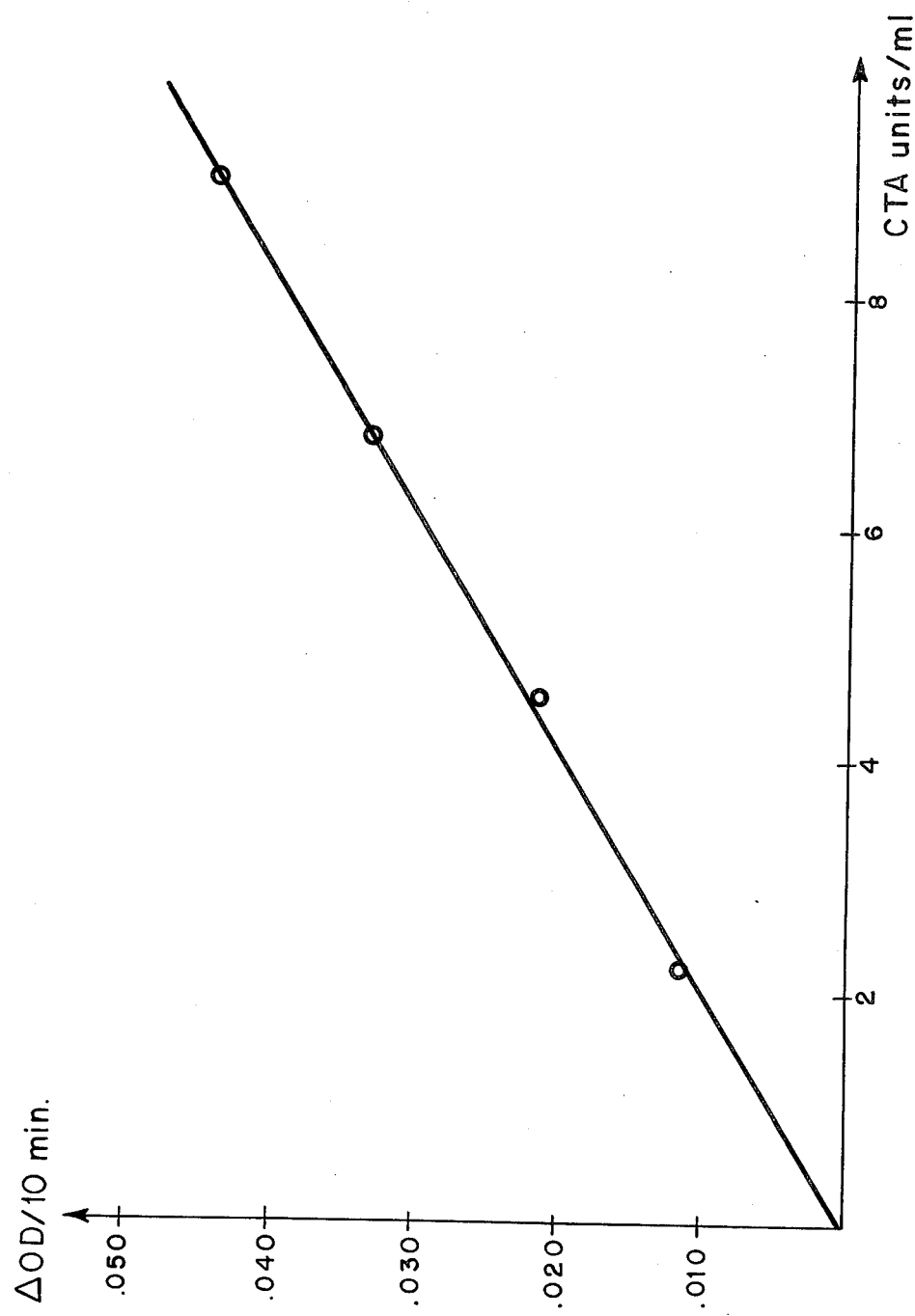

SUBSTRATE FOR THE QUANTITATIVE DETERMINATION OF PLASMINOGEN ACTIVATORS

BACKGROUND OF THE INVENTION

The present invention relates to synthetic tripeptidic substrates to be used as reagents for the quantitative determination of plasminogen activators and inhibitors thereof, plasminogen preactivators, trypsin, trypsin inhibitors and trypsinogen in human and mammal body fluids and tissue extracts by photometric, spectrophotometric and fluorescence-photometric methods.

The human organism produces several activators which cause the conversion of the proenzyme plasminogen into the active lysis enzyme plasmin. This group of activators includes e.g. tissue and blood kinase and urokinase. These activators play an important role in the mechanism of blood coagulation. If these activators are produced in an abnormally high amount, there exists the danger of an increased fibrinolytic activity and hence of an increased bleeding tendency or hemorrhage. On the other hand, too small a production of these activators causes a disturbance of the equilibrium between coagulation capacity and fibrinolysis and hence an increased danger of thrombosis. The determination of plasminogen activators in body fluids and tissue extracts is, therefore, of great importance in the clinical practice as described e.g. by I. WITT in "Biochemie der Blutgerinnung und Fibrinolyse", Verlag Chemie, Weinheim, 1975, p. 119: "The determination of the fibrinolytical activity in plasma or serum serves in the first place to recognize hyperfibrinolytic conditions which accompany various diseases. Moreover, good results were often obtained over the past years in the lysis of intravascular thrombi by the administration of plasminogen activators. Besides, measurements of the fibrinolytic activity are also imperious for checking this thrombolytic therapy.". F. E. SMYRNIOTIS et al. [Thromb. Diath. et Haemorrh., vol. III, 257–70 (1959)] report a.o. the following: "In normal persons the production of urokinase is independent of age, sex and amount of urine. The urokinase production is increased after the occurrence of a myocardium infarction and after an attack of coronary insufficiency. The production is decreased in patients suffering from carcinosis, cardial blocking and uremia. These differences suggest that significant alterations in the fibrinolytic system of the plasma may occur as a result of these diseases.".

Up to now there exist no really reliable methods for the determination of plasminogen activators in body fluids and organ extracts. Principally, three methods are known:

1. Spontaneous lysis of a blood clot. Blood is allowed to clot either spontaneously or by the addition of thrombin, and the spontaneous lysis of the clot is observed at 37° C. Lysis normally takes place only after 24 hours. This method is unspecific since the activator is not measured directly but via the lysis enzyme plasmin (cf. I. WITT, "Biochemie der Blutgerinnung und Fibrinolyse", Verlag Chemie, Weinheim, 1975, page 119).

2. Hydrolysis of casein. This method takes advantage of the property of plasmin to hydrolytically degrade casein. Casein is incubated with the sample to be tested. At the beginning and the end of the test trichloroacetic acid is added to an aliquot portion of the incubation mixture. The tyrosin content of the supernatant phase is determined by spectrophotometric measurement at 280 nm. From the tyrosin content thus determined the activator activity can be calculated approximately [cf. L. F. REMMERT et al., J. Biol. Chem. 181, 431 (1949)].

3. Esterolytic method (for urokinase). This method takes advantage of the property of urokinase to catalyse directly the hydrolysis of $N^\alpha$-acetyl-L-lysine methyl ester. This method was also used for establishing the so-called CTA urokinase unit (CTA=Committee on Thrombolytic Agents of the National Heart Institute, USA). One CTA unit is the quantity of urokinase which releases $46.2 \times 10^{-3}$ μmoles of methanol from $N^\alpha$-acetyl-L-lysine methyl ester within 1 hour at 37° C. (cf. N. U. BANG et al., "Thrombosis and Bleeding Disorders", Georg Thieme Verlag, Stuttgart, 1971, p. 377). This method can be applied exclusively to the determination of pure urokinase preparations but is not suited for the determination of urokinase in body fluids or tissue extracts since the said ester is split faster by proteolytic enzymes present therein (e.g. plasmin, plasma kallikrein, etc.) than by urokinase.

Attempts have been made to synthesize amide and peptide substrates for the determination of urokinase. However, these attempts were unsuccessful [cf. e.g., W. TROLL et al., Journal of Biological Chemistry 208, 85 (1954)].

In attempts to develop a synthetic substrate for the determination of kallikrein, the following tripeptide-p-nitroanilides Pro—Phe—Arg—pNA  and  Val—Gly—Arg—pNA

A                      B were synthesized on the grounds of theoretical considerations. These tripeptides contain the last three C-terminal amino acids of the split products formed by the action of kallikrein on kininogen. Hence, it might have been expected that these two substrates would be hydrolyzed by kallikrein which, however, was true for substrate A only. On the other hand, it was quite unexpected to find that substrate B, which is not split by kallikrein at all, is rapidly amidolytically split by urokinase and other plasminogen activators. On the grounds of these findings a new class of tripeptidic substrates was developed.

BRIEF SUMMARY OF THE INVENTION

The new substrates to which the invention relates have the following formula

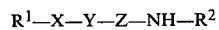

wherein X represents a group of formula

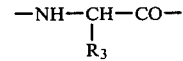

in which $R^3$ is a straight or branched alkyl radical having 1 to 7 carbon atoms or a cyclohexyl or cyclohexylmethyl radical, Y repesents a seryl group or a group of formula $—NH—(CH_2)_n—CO—$ in which n is an integer from 1 to 7, Z represents an arginyl or lysyl group, $R^1$ represents hydrogen or an acyl or sulfonyl group and $R^2$ represents an aromatic hydrocarbon radical which may optionally carry substituents.

The substrates can be protonized with a mineral acid, e.g. HCl, HBr, $H_2SO_4$, $H_3PO_4$, or an organic acid, e.g. formic, oxalic or tartaric acid.

These new substrates are particularly well suited for the quantitative determination of plasminogen activators, such as urokinase, and trypsin in human and mammal body fluids and tissue extracts. Under the action of the said biologically active factors the group —NH—$R^2$ is hydrolytically split from the substrate with formation of a colored or fluorescent split product $NH_2$-$R^2$ the quantity of which can be measured by photometric, spectrophotometric or fluorescencephotometric methods. The quantity of the product $NH_2$-$R^2$ formed per time unit is a measure of the activity of the said factors and thus permits the calculation of the quantity of a given factor present in a given test sample.

DETAILED DESCRIPTION OF THE INVENTION

The acyl group represented by $R^1$ in formula I can be characterized by the following partial formula

$R^3$—CO— wherein $R^3$ is (a) an aliphatic hydrocarbon radical which has 1 to 17 carbon atoms and which may carry an amino group in the ω-position, (b) an araliphatic hydrocarbon radical whose aliphatic radical has 1 to 17 carbon atoms and the aryl radical of which may carry an amino group, (c) a cycloaliphatic hydrocarbon radical which may carry an amino or aminomethyl group, (d) an aromatic hydrocarbon radical which may carry an alkyl, amino or aminoalkyl group, or (e) a benzyloxy group.

In particular $R^3$ can be an alkyl radical such as methyl, ethyl, propyl, butyl, pentyl, etc., up to heptadecyl. These alkyl groups can carry an amino group in the ω-position. Thus, $R^3$ can be e.g. an ω-aminopropyl, ω-aminopentyl or ω-aminononyl group. $R^3$ can furthermore be a benzyl, 2-phenylethyl, 3-phenylpropyl, etc., up to 11-phenylundecyl radical. The phenyl radical of the said groups can carry an amino group in the p-position. Thus, $R^3$ can be a p-aminobenzyl, 2-(p-aminophenyl)-ethyl, 3-(p-aminophenyl)-propyl group, etc., up to an 11-(p-aminophenyl)-undecyl group. $R^3$ can also be a cyclohexyl, 4-aminocyclohexyl, 4-aminomethylcyclohexyl, 4-aminoethylcyclohexyl, 4-aminopropylcyclohexyl or 4-aminobutylcyclohexyl group. Besides, $R^3$ can be a phenyl, α-naphthyl, β-naphthyl or biphenyl group. In turn, these groups may carry an amino, aminoalkyl or alkyl group. The alkyl of the said aminoalkyl or alkyl groups can be e.g. methyl, ethyl, propyl, isopropyl, butyl or isobutyl. Finally, $R^3$ can be an alkoxy group having 1 to 12 carbon atoms and a straight or branched chain, or an aralkyl radical the alkylene group of which has 1 to 4 carbon atoms.

The sulfonyl group represented by $R^1$ in formula I can be an alkanesulfonyl group the alkane radical of which has 1 to 12 carbon atoms and a straight or branched chain, e.g. a methane-or ethanesulfonyl group, or an arylsulfonyl group in which the aryl radical may be mono- or polycyclic and which may carry substituents, e.g. a benzenesulfonyl, p-toluenesulfonyl or 2-naphthalenesulfonyl group.

$R^2$ can be e.g. a p-nitrophenyl, 2-naphthyl or 4-methoxy-2-naphthyl group.

The invention also relates to a method for the determination of plasminogen activators, inhibitors thereof and plasminogen preactivators, and trypsin, tryspin inhibitors and trypsinogen in human and mammal body fluids and tissue extracts. This method consists in reacting the said body fluids or tissue extracts with a substrate represented by formula I and measuring by means of photometric, spectrophotometric or fluorescence-photometric methods the quantity of the split product $NH_2R^2$ formed by the hydrolytic action of the said biologically active factors on the substrate.

The substrate of the invention can be prepared by various, partly known methods:

(1) According to the first method the chromophoric groups ($R^2$ in formula I) are attached to the C-terminal amino acid group. These chromophoric groups at the same time protect the C-terminal carboxyl groups during the step-wise attachment of the amino acids in the process of building up the desired peptide chain. The other protective groups are selectively eliminated from the end product without the chromophoric group being affected. This method is described e.g. in "Peptide Synthesis" by Miklos BODANSZKY et al., Interscience Publishers, 1966, p. 163–165.

(2) According to a second method the chromophoric group is coupled to the finished peptide chain by first setting free the C-terminal carboxyl group by alkaline hydrolysis of the ester after termination of the step-wise formation of the desired peptide chain and subsequent coupling of the chromophoric group to the carboxyl group. The remaining protective groups are selectively removed under conditions whereby the chromophoric group is not affected. This method is described in "Peptide Synthesis", cf. above, pages 43 and 44.

For protecting the $N^\alpha$-amino groups during the step-wise synthesis of the peptide chains usual groups known to protect amino groups and to be split off selectively can be used. These protective groups include in the first place Cbo, MeO-Cbo, $NO_2$CbO, MCbo, BOC, TFA or formyl. The α-carboxyl group of the amino acids can be activated by several known methods, e.g. by preparing the p-nitrophenyl ester, trichlorophenyl ester, pentachlorophenyl ester, or N-hydroxysuccinimide ester derivatives and isolating these derivatives, or by preparing in situ the acid azides or anhydrides which may be either symmetrical or asymmetrical. The activation of the carboxyl group can also be achieved by means of a carbodiimide such as N,N'-dicyclohexylcarbodiimide.

The C-terminal carboxyl group in the peptide derivatives can be protected during the step-wise synthesis of the required peptide chain by means of the chromophoric amide group or by conversion into the methyl, ethyl or isopropyl ester.

The other active free groups which do not participate in the synthesis of the peptide chain can be blocked by the following methods: The δ-guanidino group of arginine is protected by $NO_2$ or Tos or simply by protonization, whereas the ε-amino group of lysine is protected by Cbo, BOC or Tos.

In the synthesis of the tripeptide chain one can proceed by first attaching the blocking group (acyl or sulfonyl group) to the N-terminal amino acid or dipeptide acid, then activating the carboxyl group of the blocked amino acid or dipeptide acid and finally attaching the obtained activated amino acid derivative or dipeptide acid derivative to the peptide derivative required for completing the peptide chain.

The preparation of the substrates of the invention according to the above methods is described in a more detailed manner in the following Examples.

The analysis of the eluates and products obtained according to the Examples was performed by thin layer chromatography. For this purpose glass plates coated with silicagel F 254 (Merck) were used. The thin layer chromatograms were developed by means of the following solvent systems:
A chloroform/methanol (9:1)
B n-propanol/ethyl acetate/water (7:1:2)
C n-butanol/acetic acid/water (3:1:1).

The chromatograms were first developed in UV light and then by reaction with chlorine/toluidine (cf. G. PATAKI, "Dünnschichtchromatographie in der Aminosäure- und PeptidChemie", Walter de Gruyter & Co., Berlin, 1966, p. 125).

The abbreviations used in the present specification and appended claims have the following meaning:
Ala = L-alanine
β-Ala = β-alanine
Arg = L-arginine
But = L-2-aminobutyric acid
4-But = 4-aminobutyric acid
Gly = glycine
Ile = L-isoleucine
D-Ile = D-isoleucine
Leu = leucine
Lys = L-lysine
NLeu = L-nor-leucine
NVal = nor-valine
Ser = L-serine
Val = L-valine
D-Val = D-valine
Ac = acetyl
Ac$_2$O = acetic acid anhydride
AcOH = acetic acid
BOC = tert.-butoxycarbonyl
Bz = benzoyl
Bzl = benzyl
Bz$_2$O = benzoic acid anhydride
Cbo = carbobenzoxy
DCCI = N,N'-dicyclohexylcarbodiimide
DCHA = dicyclohexylamine
DCU = N,N'-dicyclohexylurea
DMF = dimethylformamide
TLC = thin layer chromatography
Et$_3$N = triethylamine
HMPTA = N,N,N',N',N'',N''-hexamethylphosphoric acid triamide
SS = solvent system(s)
MCbo = p-methoxyphenylazocarbobenzoxy
MeOH = methanol
NA = naphthylamide
OtBu = tert.-butoxy
OEt = ethoxy
OisoPr = iso-propoxy
OMe = methoxy
OpNP = p-nitrophenoxy
OSu = N-succinimidoxy
pNa = p-nitroanilide
m.p. = melting point
TFA = trifluoroacetyl
Tos = p-toluenesulfonyl

EXAMPLE 1

I. N$^\alpha$-Bz-Val-Gly-Arg-pNA.HCl (Ia) N$^\alpha$-Cbo-Arg(NO$_2$)-pNA (1) In a 500 ml three-necked flask 32.55 g (92.1 mmoles) of well dried Cbo-Arg(NO$_2$)-OH were dissolved at 20° C. in 200 ml of N,N,N',N',N'',N''-hexamethylphosphoric acid triamide which had been dried over P$_2$O$_5$ and freshly distilled, while keeping the atmosphere in the flask moisture-free. To the solution were added first 9.32 g (92.1 mmoles) of Et$_3$N and then portionwise 18.90 g (115.1 mmoles) of p-nitrophenyl isocyanate (25% excess). The reaction solution was kept at room temperature for 24 hours and then added dropwise, while stirring, to 1.5 liters of aqueous 2% NaHCO$_3$ solution. The precipitated product was isolated by filtration and washed three times with portions of 0.7 liter of aqueous 2% NaHCO$_3$ solution, three times with portions of 0.7 liter of distilled water, three times with portions of 0.5 liter of 0.5N HCl and finally three times with portions of 0.5 liter of distilled water. The product was then dried in vacuo at 40° C. and then extracted twice with portions of 200 ml of boiling MeOH. The major portion of N$^\alpha$-Cbo-ωnitroarginyl lactam formed as a by-product, but only a minute quantity of the desired product were thus dissolved. The obtained pre-purified product was dried and then extracted twice with portions of 50 ml of DMF heated to 70° C. The desired product was thus completely dissolved, whereas the by-product, N,N'-bis-p-nitrophenylurea remained undissolved. The DMF solution was concentrated in vacuo at 40° C. The addition of MeOH caused crystallization of a substance which was chromatographically homogeneous in SS A and B and which had an m.p. of 186°–188.5° C. Yield: 29.75 g (68.2% of the theory).

Elementary analysis and calculation from the empirical formula C$_{20}$H$_{23}$N$_7$O$_7$ gave the following values (the values for the empirical formula are put within brackets): C=50.42% (50.74%); H=4.98% (4.90%); N=20.90% (20.71%). $[\alpha]_D^{22}$=1.27° (c=1.0; AcOH).

(2) In a 500 ml three-necked flask 17.7 g (50 mmoles) of dried Cbo-Arg(NO$_2$)-OH were dissolved in 350 ml of THF/DMF (1:1), and then 5.05 g (50 mmoles) of Et$_3$N were added to the solution, while the atmosphere in the flask was kept moisture-free. After cooling of the reaction solution to −10° C., 6.85 g (50 mmoles) of isobutyl chloroformate dissolved in 30 ml of THF were added dropwise thereto within 15 minutes at a temperature kept between −10° and −5° C. After about 10 minutes a solution of 8.2 g (50 mmoles) of p-nitroaniline in 15 ml of DMF was added dropwise, again at a temperature kept between −10° and −5° C. After 2 hours the cooling was interrupted, and the reaction mixture was allowed to stand for 24 hours at room temperature. The solvent was removed by distillation in vacuo. The residue was washed three times with distilled water, three times with aqueous 5% NaHCO$_3$ solution and again three times with distilled water. After drying in vacuo the crude product was dissolved in MeOH, and the solution was passed through a column of "Sephadex LH-20" (cross-linked dextran gel) equilibrated with MeOH. A fraction of the eluate yielded 7.67 g (32.4% of the theory) of a product which had the same physical properties as the product prepared according to paragraph (1).

(3) 17.7 g (50 mmoles) of Cbo-Arg(NO$_2$)—OH were dissolved in 75 ml of DMF. After cooling to −10° C., 10.3 g (50 mmoles) of DCCI and 8.2 g (50 mmoles) of p-nitroaniline were added to the solution. After 4 hours at −10° C. and 20 hours at 20° C. the precipitated DCU was removed by filtration, and the filtrate was concentrated to dryness. After dissolution of the crude product in MeOH the solution was passed through a column of "Sephadex LH-20" equilibrated with MeOH. From a fraction of the eluate a major proportion of by-product, i.e. N-Cbo-Arg(NO$_2$)-N,N'-dicyclohexylurea, and 4.32 g (17.9% of the theory) of the desired product were obtained. This product had the same physical properties as the product prepared according to paragraph (1).

(Ib) N$^\alpha$-Cbo-Gly-Arg(NO$_2$)-pNA

In a flask 9.5 g (20 mmoles) of N$^\alpha$-Cbo-Arg(NO$_2$)-pNA (cf. Example (1a)) were treated, while stirring, with 80 ml of 2N HBr in glacial acetic acid within 1 hour at 20° C. in the absence of moisture. The substance dissolved with CO$_2$ evolution. The reaction solution was slowly added dropwise with vigorous stirrer, to 600 ml of anhydrous ether. This resulted in the precipitation of HBr.H-Arg(NO$_2$)-pNA. The ethereal phase was sucked off through a filter rod. The remaining precipitate was washed four times with portions of 150 ml of dry ether in order to remove benzyl bromide which had formed as well as excess HBr and AcOH. After drying over NaOH platelets in vacuo the deblocked product was obtained in a quantitative yield. The dry hydrobromide derivative was dissolved in 50 ml of DMF. After cooling of the solution to −10° C., 4.16 ml (30 mmoles) of Et$_3$N were added thereto in order to release H-Arg(NO$_2$)-pNA from the hydrobromide. The Et$_3$N.HBr salt which had formed was sucked off and washed with a small quantity of cold DMF. 6.94 g (21 mmoles) of Cbo-Gly-OpNP were added to the filtrate at −10° C. After a few hours the reaction solution had reached room temperature. The solution was again cooled to −10° C. and then buffered with 1.4 ml (10 mmoles) of Et$_3$N. After about 5 hours a further 1.4 ml of Et$_3$N was added. After further 24 hours the reaction solution was concentrated to dryness in vacuo at 40° C. The residue was digested three times with portions of 100 ml of distilled water and then again dried in vacuo over NaOH platelets at 40° C. The dried product was recrystallized from MeOH to obtain 6.77 g of a product which was homogeneous according to TLC in the SS A and B. After gel filtration of the mother liquor through a column of "Sephadex LH-20" equilibrated with MeOH a further crop of 4.29 g of the same product was obtained. Thus, a total of 11.06 g (87.7% of the theory) of homogeneous product having an m.p. of 159°–161° C. was obtained.

Elementary analysis and calculation from the empirical formula C$_{22}$H$_{26}$N$_8$O$_8$ gave the following values (the values from the empirical formula are put within brackets): C=50.07% (C=49.81%); H=4.99% (H=4.94%); N=21.48% (N=21.12%).

(Ic) N$^\alpha$-Cbo-Val-Gly-Arg(NO$_2$)-pNA 10.6 g (20 mmoles) of N$^\alpha$-Cbo-Gly-Arg(NO$_2$)-pNA (cf. Example (Ib)) were treated with 120 ml of 2N HBr in glacial acetic acid (0.24 mole) as described in Example (Ib). After drying in vacuo over NaOH platelets the dry hydrobromide of the dipeptide derivative was dissolved in 50 ml of DMF. After cooling 3.04 g of the Et$_3$N dissolved in 10 ml of DMF (30 mmoles) were added to the solution. The Et$_3$N.HBr which had formed was removed by filtration and washed with a small quantity of cold DMF. To the filtrate 8.20 g (22 mmoles) of Cbo-Val-OpNP were added. The reaction product was treated in the manner described in Example (Ib). By gel filtration through a column of "Sephadex LH-20" equilibrated with MeOH and elution with MeOH, 10.95 g (87.0% of the theory) of a product which was homogeneous according to TLC in the SS A and B and which had an m.p. of 212°–214° C. were obtained.

Elementary analysis and calculation from the empirical formula C$_{27}$H$_{35}$N$_9$O$_9$ gave the following values: C=52.01% (51.50%); H=5.68% (5.60%); N=20.27% (20.02%). (The values from the empirical formula are put within brackets.)

(Id) N$^\alpha$-Bz-Val-Gly-Arg(NO$_2$)-pNA 10.90 g (17.3 mmoles) of N$^\alpha$-Cbo-Val-Gly-Arg(NO$_2$)-pNA (cf. Example Ic)) were treated with 70 ml of 2N HBr in glacial acetic acid (0.14 mole). The reaction mixture was further treated in the manner described in Example (Ib).

The dried tripeptide-hydrobromide derivative was dissolved in 60 ml of DMF. After cooling 3.60 ml (26 mmoles) of Et$_3$N were added to the solution. The Et$_3$N.HBr which had formed was removed by filtration and washed with a small quantity of cold DMF. To the filtrate 6.66 g (29.4 mmoles) of benzoic acid anhydride were added. The reaction solution was buffered and then further treated in the manner described in Example (Ib). The dried product was recrystallized from MeOH to give 4.28 g of a substance which was homogeneous according to TLC in the SS A and B and which had an m.p. of 222°–223° C. A further crop of 3.75 g of product having an m.p. of 222°–223° C. was obtained from the mother liquors by gel filtration through a column of "Sephadex LH-20" equilibrated with MeOH. Thus, a total of 8.03 g (77.4% of the theory) of homogeneous product was obtained.

Elementary analysis and calculation from the empirical formula C$_{26}$H$_{33}$N$_9$O$_8$ gave the following values: C=51.88% (52.08%); H=5.63% (5.55%); N=21.56% (21.03%).

I. N$^\alpha$-Bz-Val-Gly-Arg-pNA.HCl 6.044 g (10.08 mmoles) of N$^\alpha$-Bz-Val-Gly-Arg(NO$_2$)-pNA (cf. Example (Id)) were weighed in in an Erlenmeyer flask. Then 81 ml of 1-molar boron tris-trifluoroacetate in trifluoroacetic acid were added. The reaction was allowed to proceed for 2 hours at 0° C. and then for 22 hours at 20° C., whereupon the protective nitro group was removed, while stirring, with the exclusion of humidity. The reaction solution was concentrated to dryness in vacuo, and the residue was taken up in MeOH. In order to convert the peptide derivative into its hydrochloride salt 1.0 ml of concentrated HCl was added to the solution. The solution was concentrated to dryness in vacuo. After having repeated these operations three times the residue was dissolved in 200 ml of 30% aqueous AcOH. The AcOH solution was purified on a column of "Sephadex G-15" equilibrated with 30% aqueous AcOH and eluted with 30% aqueous AcOH. That fraction of the AcOH eluate which was split by treatment with trypsin with liberation of p-nitroaniline was freeze-dried after the addition of 0.85 ml (10.1 mmoles) of conc. HCl. There were thus obtained 4.75 g (79.7% of the theory) of an amorphous powder which was homogeneous according to TLC in the SS C.

Elementary analysis and calculation from the empirical formula $C_{26}H_{35}N_8O_6Cl$ gave the following values: C=52.71% (52.83%); H=5.88% (5.97%); N=19.07% (18.96%) and Cl=5.95% (6.00%).

The amino acid analysis confirmed the presence of the expected amino acids in the correct proportions: Arg: 0.97—Gly: 1.0—Val: 0.98.

EXAMPLE 2

II. H-Val-Gly-Arg-pNA.2HCl 630 mg (1 mmole) of $N^{\alpha}$-Cbo-Val-Gly-Arg(NO$_2$)-pNA prepared according to Example 1, paragraph Ic), were weighed in in the reaction vessel of a Sakakibara apparatus. 10 ml of dry hydrofluoric acid gas were condensed in the reaction vessel. The reaction was allowed to proceed for 1 hour at 0° C., and then the protective $N^{\alpha}$-carbobenzoxy group as well as the protective nitro group of arginine were removed, while stirring. The condensed hydrofluoric acid gas was removed by distillation in vacuo, and the residue was dissolved in DMF. In order to convert the peptide derivative into its hydrochloride salt 0.2 ml of concentrated HCl was added to the solution, and the solution was concentrated to dryness. After having repeated twice these operations the residue was dissolved in 25 ml of 30% aqueous AcOH. The AcOH solution was purified on a column of "Sephadex G-15" equilibrated with 30% aqueous AcOH and eluted with 30% of aqueous AcOH. That fraction of the AcOH eluate which was split by treatment with trypsin with liberation of p-nitroaniline was freeze-dried after the addition of 160 μl (2 mmoles) of conc. HCl. There were thus obtained 360 mg (68.8% of the theory) of an amorphous powder which was homogeneous according to TLC in the SS C.

Elementary analysis and calculation from the empirical formula $C_{19}H_{32}N_8O_5Cl_2$ gave the following values: C=43.85% (43.60%); H=6.23% (6.16%); N=21.65% (21.41%) and Cl=13.42% (13.55%).

The amino acid analysis confirmed the presence of the expected amino acids in the correct proportions: Arg: 0.98—Gly: 1.00—Val: 0.96.

EXAMPLE 3

III. $N^{\alpha}$-Bz-Ile-Gly-Arg-pNA.HCl (IIIa) $N^{\alpha}$-Cbo-Ile-Gly-Arg(NO$_2$)-pNA 5.3 g (10 mmoles) of the compound prepared according to Example 1, paragraph (Ib), were deblocked by the method described in Example 1, paragraph (Ib), and then dissolved in 35 ml of DMF. 2.08 ml (15 mmoles) of Et$_3$N were added to the solution. After cooling to −10° C. the Et$_3$N.HBr which had formed was removed by filtration and washed with a small quantity of cold DMF. 4.25 g (11 mmoles) of Cbo-Ile-OpNP were added to the filtrate, and the reaction solution was further treated according to Example 1, paragraph (Ib). After gel filtration on "Sephadex LH-20" in MeOH there were obtained 5.50 g (85.5% of the theory) of crystalline compound IIIa which melted at 197°-200° C. and was homogeneous according to TLC in the SS A and B.

Elementary analysis and calculation from the empirical formula $C_{28}H_{37}N_9O_9$ gave the following values: C=51.98% (52.25%); H=5.91% (5.79%) and N=19.73% (19.59%).

(IIIb) $N^{\alpha}$-Bz-Ile-Gly-Arg(NO$_2$)-pNA 1.29 g (2 mmoles) of the compound prepared according to Example 3, paragraph (IIIa), were deblocked by the method described in Example 1, paragraph (Ib), dissolved in 15 ml of DMF, and 420 μl (3 mmoles) of Et$_3$N were added to the solution. After cooling to −10° C., 680 mg (3 mmoles) of Bz$_2$O were added to the solution. The reaction solution was then further treated according to Example 1, paragraph (Ib). After gel filtration on "Sephadex LH-20" in MeOH there were obtained 1.05 g (85.6% of the theory) of amorphous substance (IIIb) which was homogeneous according to TLC in the SS A and B.

Elementary analysis and calculation from the empirical formula $C_{27}H_{35}N_9O_8$ gave the following values: C=52.54% (52.85%); H=5.85% (5.75%) and N=20.68 (20.54%).

III. $N^{\alpha}$-Bz-Ile-Gly-Arg-pNA.HCl 614 mg (1 mmole) of the compound prepared according to Example 3, paragraph (IIIb), were weighed in in the reaction vessel of a Sakakibara apparatus. 10 ml of dry hydrofluoric acid gas were condensed in the reaction vessel. The reaction was allowed to proceed for 1 hour at 0° C., while stirring, and then the protective nitro group was removed, while stirring. The condensed hydrofluoric acid gas was removed from the reaction mixture by distillation in vacuo, and the residue was dissolved in DMF. In order to convert the peptide derivative into its HCl salt 0.2 ml (∼2.5 mmoles) of conc. HCl were added, and the solution was concentrated to dryness. After having repeated twice these operations the residue was dissolved in 50 ml of 30% AcOH. The AcOH solution was purified on a column of "Sephadex G-15" equilibrated with 30% AcOH and eluted with 30% AcOH. That fraction of the AcOH eluate which was split by treatment with trypsin with liberation of p-nitroaniline was freeze-dried after the addition of 80 μl (1 mmole) of conc. HCl. There were thus obtained 505 mg (83.5% of the theory) of an amorphous powder which was homogeneous according to TLC in the SS C.

Elementary analysis and calculation from the empirical formula $C_{27}H_{37}N_8O_6Cl$ gave the following values: C=53.28% (53.59%); H=6.21% (6.16%); N=18.70% (18.52%) and Cl=5.82% (5.86%).

The amino acid analysis confirmed the presence of the expected amino acids in the correct proportions: Arg: 0.96—Gly: 1.00—Ile: 0.98.

EXAMPLE 4

IV. $N^{\alpha}$-Bz-Leu-Gly-Arg-pNA.HCl (IVa) $N^{\alpha}$-Cbo-Leu-Gly-Arg(NO$_2$)-pNA 2.65 g (5 mmoles) of the compound prepared according to Example 1, paragraph (Ib), were deblocked according to Example 1, paragraph (Ib), dissolved in 25 ml of DMF, and 1.04 ml (7.5 mmoles) of Et$_3$N were added to the solution. After cooling to −10° C. the Et$_3$N.HBr which had formed was removed by filtration and washed with a small quantity of cold DMF. 2.13 g (5.5 mmoles) of Cbo-Leu-OpNP were added to the obtained filtrate and the reaction solution was further treated according to Example 1, paragraph (Ib). After gel filtration on "Sephadex LH-20" in MeOH there were obtained 2.85 g (88.6% of the theory) of the crystalline compound IVa which melted at 189°–191° C. and was homogeneous according to TLC in the SS A and B.

Elementary analysis and calculation from the empirical formula $C_{28}H_{37}N_9O_9$ gave the following values: C=52.05% (52.25%); H=5.79% (5.79%) and N=19.91% (17.59%).

(IVb) $N^{\alpha}$-Bz-Leu-Gly-Arg($NO_2$)-pNA 1.29 g (2 mmoles) of the compound prepared according to Example 4, paragraph (IVa), were deblocked according to Example 1, paragraph (Ib), dissolved in 15 ml of DMF, and 420 μl (3 mmoles) of $Et_3N$ were added to the solution. After cooling to −10° C., 680 mg (3 mmoles) of $Bz_2O$ were added to the reaction mixture, and the reaction solution was further treated according to Example 1, paragraph (Ib). After gel filtration on "Sephadex LH-20" in MeOH there were obtained 0.99 g (80.7% of the theory) of the amorphous compound (IVb) which was homogeneous according to TLC in the SS A and B.

Elementary analysis and calculation from the empirical formula $C_{27}H_{35}N_9O_8$ gave the following values: C=52.49% (52.85%); H=5.81% (5.75%) and N=20.59% (20.54%).

IV. $N^{\alpha}$-Bz-Leu-Gly-Arg-pNA.HCl 614 mg (1 mmole) of the compound prepared according to Example 4, paragraph (IVb), were reacted according to Example 2, paragraph II, to form compound IV. Purification: gel filtration on "Sephadex G-15" in 30% AcOH. Yield: that fraction of the AcOH eluate which was split by treatment with trypsin with liberation of p-nitroaniline was freeze-dried after the addition of 80 μl (1 mmole) of conc. HCl. There were thus obtained 508 mg ((84.0% of the theory) of an amorphous powder which was homogeneous according to TLC in the SS C.

Elementary analysis and calculation from the empirical formula $C_{27}H_{37}N_8O_6Cl$ gave the following values: C=53.75% (53.59%); H=6.21% (6.16%); N=18.74% (18.52%) and Cl=5.76% (5.86%).

The amino acid analysis confirmed the presence of the expected amino acids in the correct proportions: Arg: 0.97—Gly: 1.00—Leu: 1.02.

EXAMPLE 5

V. $N^{\alpha}$-Bz-Val-Ser-Arg-pNA.HCl

(Va) $N^{\alpha}$-BOC-Ser(OBzl)-Arg($NO_2$)-pNA 3.55 g (7.5 mmoles) of the compound prepared according to Example 1, paragraph (Ia), were deblocked according to Example 1, paragrah (Ib), dissolved in 35 ml of DMF, and 1.56 ml (11.3 mmoles) of $Et_3N$ were added to the solution. After cooling to −10° C. the $Et_3N$.HBr which had formed was removed by filtration and washed with a small quantity of cold DMF. 3.35 g (8 mmoles) of BOC-Ser(OBzl)-OpNP were added to the obtained filtrate, and the reaction solution was further treated according to Example 1, paragraph (Ib). After gel filtration on "Sephadex LH-20" in MeOH there were obtained 4.09 g (88.4% of the theory) of the partially crystalline compound Va which was homogeneous according to TLC in the SS A and B.

Elementary analysis and calculation from the empirical formula $C_{27}H_{36}N_8O_9$ gave the following values: C=52.82% (52.59%); H=5.78% (5.88%) and N=18.30% (18.17%).

(Vb) $N^{\alpha}$-BOC-Val-Ser(OBzl)-Arg($NO_2$)-pNA 3.08 mg (5 mmoles) of the compound prepared according to Example 5, paragraph (Va), were weighed in in an Erlenmeyer flask, and 15 ml of trifluoroacetic acid were added thereto in a moisturefree atmosphere. The substance dissolved with evolution of $CO_2$, while stirring for 30 minutes at 20° C. The reaction solution was slowly added dropwise, while vigorously stirring, to 250 ml of dry ether which resulted in the precipitation of $CF_3COOH$.H-Ser(OBzl)-Arg($NO_2$)-pNA. The ethereal phase was sucked off with a filter rod. The remaining precipitate was treated three more times with portions of 50 ml of dry ether in order to remove the tert. butanol which had formed and the excess trifluoroacetic acid. After drying in vacuo over NaOH platelets the deblocked product was obtained in an almost quantitative yield. The dried trifluoroacetate derivative was dissolved in 25 ml of DMF, cooled to −10° C., and 1.04 ml (7.5 mmoles) of $Et_3N$ were added to the solution in order to release H-Ser(OBzl)-Arg($NO_2$)-pNA from the trifluoroacetate. Then 1.73 g (5.5 mmoles) of BOC-Val-OSu were added. The reaction solution was allowed to stand for a few hours and had meanwhile reached room temperature. It was again cooled to −10° C. and buffered with 0.35 ml (2.5 mmoles) of $Et_3N$. After about five hours another 0.35 ml of $Et_3N$ was added. After a further 24 hours the reaction solution was concentrated to dryness in vacuo. The residue was further treated according to Example 1, paragraph (Ib). After gel filtration on "Sephadex LH-20" in MeOH there were obtained 2.81 g (78.5% of the theory) of an amorphous powder which was homogeneous according to TLC in the SS A and B.

Elementary analysis and calculation from the empirical formula $C_{32}H_{45}N_9O_{10}$ gave the following values: C=54.03% (53.70%); H=6.40% (6.34%) and N=17.88% (17.61%).

(Vc) $N^{\alpha}$-Bz-Val-Ser(OBzl)-Arg($NO_2$)-pNA 716 mg (1 mmole) of the compound prepared according to Example 5, paragraph (Vb), were deblocked according to Example 5, paragraph (Vb), dissolved in 8 ml of DMF, and 210 μl (1.5 mmoles) of $Et_3N$ were added to the solution. After cooling to −10° C., 450 mg (2 mmoles) of $Bz_2O$ were added, and the reaction solution was further treated according to Example 1, paragraph (Ib). After gel filtration on "Sephadex LH-20" in MeOH there were obtained 532 mg (73.9% of the theory) of crystalline compound Vc which melted at 175°–178° C. and was homogeneous according to TLC in the SS A and B.

Elementary analysis and calculation from the empirical formula $C_{34}H_{41}N_9O_9$ gave the following values: C=56.65% (56.74%); H=5.69% (5.74%) and N=17.83% (17.52%).

V. $N^{\alpha}$-Bz-Val-Ser-Arg-pNA.HCl 360 mg (0.5 mmole) of the compound prepared according to Example 5, paragraph (Vc), were reacted according to Example 2, paragraph II, to form compound V. Purification: gel filtration on "Sephadex G-15" in 30% AcOH. Yield: that fraction of the AcOH eluate which was split by treatment with trypsin with liberation of p-nitroaniline was freeze-dried after the addition of 40 μl (0.5 mmole) of conc. HCl. There were thus obtained 160 mg (51.5% of the theory) of an amor-

EXAMPLE 6

VI. N$^\alpha$-Bz-Ile-Ser-Arg-pNA.HCl (VIa) N$^\alpha$-BOC-Ile-Ser(OBzl)-Arg(NO$_2$)-pNA 1.54 g (2.5 mmoles) of the compound prepared according to Example 5, paragraph (Va), were deblocked according to Example 5, paragraph (Vb), dissolved in 15 ml of DMF, and 520 μl (3.75 mmoles) of Et$_3$N were added to the solution. After cooling to −10° C., 905 mg (2.75 mmoles) of BOC-Ile-OSu were added and the reaction solution was further treated according to Example 1, paragraph (Ib). After gel filtration on "Sephadex LH-20" in MeOH there were obtained 1.45 g (79.5% of the theory) of the amorphous compound VIa which was homogeneous according to TLC in the SS A and B.

Elementary analysis and calculation from the empirical formula C$_{33}$H$_{47}$N$_9$O$_{10}$ gave the following values: C=54.82% (54.31%); H=6.52% (6.49%) and N=17.35% (17.27%).

(VIb) N$^\alpha$-Bz-Ile-Ser(OBzl)-Arg(NO$_2$)-pNA 730 mg (1 mmole) of the compound prepared according to Example 6, paragraph (VIa), were deblocked according to Example 5, paragraph (Vb), and dissolved in 7 ml of DMF. After cooling to −10° C., 210 μl (1.5 mmoles) of Et$_3$N and immediately afterwards 450 mg (2 mmoles) of Bz$_2$O were added to the solution. The reaction solution was further treated according to Example 1, paragraph (Ib). After gel filtration on "Sephadex LH-20" in MeOH there were obtained 615 mg (83.8% of the theory) of the amorphous compound VIb which was homogeneous according to TLC in the SS A and B.

Elementary analysis and calculation from the empirical formula C$_{35}$H$_{43}$N$_9$O$_9$ gave the following values: C=57.61% (57.29%); H=6.01% (5.91%) and N=17.53% (17.18%).

VI. N$^\alpha$-Bz-Ile-Ser-Arg-pNA.HCl 367 mg (0.5 mmole) of the compound prepared according to Example 6, paragraph (VIb), were reacted according to Example 2, paragraph II, to form compound VI. Purification: gel filtration on "Sephadex G-15" in 30% AcOH. Yield: that fraction of the AcOH eluate which was split by treatment with trypsin with liberation of p-nitroaniline was freeze-dried after the addition of 40 μl (0.5 mmole) of conc. HCl. There were obtained 168 g (45.8% of the theory) of an amorphous powder which was homogeneous according to TLC in the SS C.

Elementary analysis and calculation from the empirical formula C$_{28}$H$_{39}$N$_8$O$_7$Cl gave the following values: C=53.21% (52.95%); H=6.26% (6.19%); N=17.88% (17.64%) and Cl=5.57% (5.58%).

The amino acid analysis confirmed the presence of the expected amino acids in the correct proportions: Arg: 0.96—Ser: 0.95—Ile: 1.00.

EXAMPLE 7

VII. N$^\alpha$-Bz-Leu-Ser-Arg-pNA.HCl (VIIa) N$^\alpha$-BOC-Leu-Ser(OBzl)-Arg(NO$_2$)-pNA 1.55 g (2.5 mmoles) of the compound prepared according to Example 5, paragraph (Va), were deblocked according to Example 5, paragraph (Vb), dissolved in 15 ml of DMF, and 520 μl (3.75 mmoles) of Et$_3$N were added to the solution. After cooling to −10° C., 0.91 g (2.78 mmoles) of BOC-Leu-OSu were added, and the reaction solution was further treated according to Example 1, paragraph (Ib). After gel filtration on "Sephadex LH-20" in MeOH there were obtained 1.44 g (78.9% of the theory) of the amorphous compound VIIa which was homogeneous according to TLC in the SS A and B.

Elementary analysis and calculation from the empirical formula C$_{33}$H$_{47}$N$_9$O$_{10}$ gave the following values: C=54.70% (54.31%); H=6.55% (6.49%) and N=17.43% (17.27%).

(VIIb) N$^\alpha$-Bz-Leu-Ser(OBzl)-Arg(NO$_2$)-pNA 1.46 g (2 mmoles) of the compound prepared according to Example 7, paragraph (VIIa), were deblocked according to Example 5, paragraph (Vb), and dissolved in 15 ml of DMF. After cooling to −10° C., 420 μl (3 mmoles) of Et$_3$N and immediately afterwards 0.90 g (4 mmoles) of Bz$_2$O were added to the solution. The reaction solution was further treated according to Example 1, paragraph (Ib). After gel filtration on "Sephadex LH-20" in MeOH there were obtained 1.25 g (85.2% of the theory) of the amorphous compound (VIIb) which was homogeneous according to TLC in the SS A and B.

Elementary analysis and calculation from the empirical formula C$_{35}$H$_{43}$N$_9$O$_9$ gave the following values: C=57.38% (57.29%); H=5.98% (5.91%) and N=17.57% (17.18%).

VII. N$^\alpha$-Bz-Leu-Ser-Arg-pNA.HCl 735 mg (1 mmole) of the compound prepared according to Example 7, paragraph (VIIb), were reacted according to Example 2, paragraph II, to form compound VII. Purification: gel filtration on "Sephadex G-15" in 30% AcOH. Yield: that fraction of the AcOH eluate which was split by treatment with trypsin with liberation of p-nitroaniline was freeze-dried after the addition of 80 μl (1 mmole) of conc. HCl. There were obtained 355 mg (55.9% of the theory) of an amorphous powder which was homogeneous according to TLC in the SS C.

Elementary analysis and calculation from the empirical formula C$_{28}$H$_{39}$N$_8$O$_7$Cl gave the following values: C=53.09% (52.95%); H=6.09% (6.19%); N=17.91% (17.64%) and Cl=5.49% (5.58%).

The amino acid analysis confirmed the presence of the expected amino acids in the correct proportions: Arg: 0.95—Ser: 0.93—Leu: 1.00.

EXAMPLE 8

VIII. N$^\alpha$-3-Phenylpropionyl-Val-Gly-Arg-pNA.HCl (VIIIa)

N$^\alpha$-3-Phenylpropionyl-Val-Gly-Arg(NO$_2$)-pNA 3.15 g (5 mmoles) of the compound prepared according to Example 1, paragraph (Ic), were deblocked according to Example 1, paragraph (Ib), and dissolved in 25 ml of DMF. After cooling to −10° C., 1.05 ml (7.5 mmoles) of Et$_3$N and then 1.50 g (5.5 mmoles) of p-nitrophenyl 3-phenylpropionate were added to the solution. The reaction solution was further treated according to Example 1, paragraph (Ib). After gel filtration on "Sephadex LH-20" in MeOH there were obtained 2.75 g (87.6% of the theory) of crystalline compound VIIIa which melted at 216°–218° C. and was homogeneous according to TLC in the SS A and B.

Elementary analysis and calculation from the empirical formula C$_{28}$H$_{37}$N$_9$O$_8$ gave the following values: C=53.38% (53.58%); H=6.02% (5.94%) and N=20.40% (20.09%).

VIII. N$^\alpha$-3-Phenylpropionyl-Val-Gly-Arg-pNA.HCl 1.26 g (2 mmoles) of the compound prepared according to Example 8, paragraph (VIIIa), were reacted according to Example 1, paragraph I, to form compound VIII. Purification: gel filtration on "Sephadex G-15" in 30% AcOH. Yield: that fraction of the AcOH eluate which was split by treatment with trypsin with liberation of p-nitroaniline was freeze-dried after the addition of 160 μl (2 mmoles) of conc. HCl. There were thus obtained 1.12 g (90.4% of the theory) of an amorphous powder which was homogeneous according to TLC in the SS C.

Elementary analysis and calculation from the empirical formula C$_{28}$H$_{39}$N$_8$O$_6$Cl gave the following values: C=54.58% (54.32%); H=6.29% (6.35%); N=18.40% (18.10%) and Cl=5.67% (5.73%).

The amino acid analysis confirmed the presence of the expected amino acids in the correct proportions: Arg: 0.96—Gly: 1.00—Val: 1.02.

EXAMPLE 9

IX. N$^\alpha$-2-Phenylacetyl-Val-Gly-Arg-pNA.HCl (IXa) N$^\alpha$-2-Phenylacetyl-Val-Gly-Arg(NO$_2$)-pNA 1.57 g (2.5 mmoles) of the compound prepared according to Example 1, paragraph (Ic), were deblocked according to Example 1, paragraph (Ib), and dissolved in 15 ml of DMF. After cooling to −10° C., 520 μl (3.75 mmoles) of Et$_3$N and then 710 mg (2.75 mmoles) of p-nitrophenyl 2-phenylacetate were added to the solution. The reaction solution was further treated according to Example 1, paragraph (Ib). After gel filtration on "Sephadex LH-20" in MeOH there were obtained 1.35 g (88.0% of the theory) of crystalline compound IXa which melted at 184° C. and was homogeneous according to TLC in the SS A and B.

Elementary analysis and calculation from the empirical formula C$_{27}$H$_{35}$N$_9$O$_8$ gave the following values: C=53.09% (52.85%); H=5.82% (5.75%) and N=20.91% (20.54%).

IX. N$^\alpha$-2-Phenylacetyl-Val-Gly-Arg-pNA.HCl 615 mg (1 mmole) of the compound prepared according to Example 9, paragraph IXa), were reacted according to Example 1, paragraph I, to form compound IX. Purification: gel filtration on "Sephadex G-15" in 30% AcOH. Yield: that fraction of the AcOH eluate which was split by treatment with trypsin with liberation of p-nitroaniline was freeze-dried after the addition of 80 μl (1 mmole) of conc. HCl. There were thus obtained 515 mg (85.1% of the theory) of an amorphous powder which was homogeneous according to TLC in the SS C.

Elementary analysis and calculation from the empirical formula C$_{27}$H$_{37}$N$_8$O$_6$Cl gave the following values: C=53.19% (53.59%); H=6.21% (6.16%); N=18.77% (18.52%) and Cl=5.75% (5.86%).

The amino acid analysis confirmed the presence of the expected amino acids in the correct proportions: Arg: 0.94—Gly: 1.00—Val. 0.98.

EXAMPLE 10

X. N$^\alpha$-Cbo-C.Cyclohexylglycyl-Gly-Arg-pNA.2HCl (Xa) N$^\alpha$-Cbo-Arg-pNA.HCl In a 250 ml three-necked flask 16.0 g (47.0 mmoles) of CboArg-OH.HCl dried in vacuo over P$_2$O$_5$ were dissolved in 90 ml of absolute HMPTA at 20° C. with the exclusion of humidity. To the resulting solution there were added at room temperature first a solution of 4.74 g (47.0 mmoles) of Et$_3$N in 10 ml of HMPTA and then portionwise 16.4 g (100 mmoles) of p-nitrophenyl isocyanate (100% excess). After 24 hours' reaction time at 20° C. the major amount of the HMPTA was removed by distillation in vacuo. The residue was extracted several times with 30% AcOH. The residue was discarded. The combined AcOH extracts were further purified by gel filtration on a "Sephadex G-15" column equilibrated with 30% AcOH and eluted with 30% AcOH. The fraction of the AcOH eluate which was split by treatment with trypsin with liberation of p-nitroaniline was freeze-dried. There were obtained 12.6 g of an amorphous powder which was homogeneous in the SS C as shown by TLC.

Elementary analysis and calculation from the empirical formula C$_{20}$H$_{25}$N$_6$O$_5$Cl gave the following values: C=51.29% (51.67%), H=5.48% (5.42%), N=17.92% (18.08%), Cl=7.50% (7.63%).

(Xb) N$^\alpha$-Cbo-Gly-Arg-pNA.HBr 4.65 g (10 mmoles) of compound (Xa) were treated at 20° C. for 45 minutes, while stirring, with 40 ml of 2 N HBr in glacial acetic acid in the absence of moisture. The amino acid derivative dissolved with CO$_2$ evolution. The reaction solution was added dropwise, with vigorous stirring, to 250 ml of absolute ether. This resulted in the precipitation of (2HBr).H-Arg-pNA. The ethereal phase was sucked off, and the solid phase was washed 4 times with portions of 100 ml of absolute ether in order to remove the benzyl bromide which had formed as a by-product and the excess HBr and AcOH. After drying over NaOH platelets in vacuo the deblocked product was obtained in a quantitative yield. The dry (2HBr).H-Arg-pNA was dissolved in 25 ml of DMF. 1.40 ml (10 mmoles) of Et$_3$N were added to the solution cooled to −10° C. A precipitate of Et$_3$N.HBr formed which was removed by filtration and washed with a small amount of cold DMF. 3,65 g (11 mmoles) of Cbo-Gly-OpNP were added to the filtrate at −10° C. After a few hours the reaction solution had reached a temperature of 20° C. The solution was again cooled to −10° C. and buffered with 0.35 ml (2.5 mmoles) of Et$_3$N. 16 hours later another 0.35 ml of Et$_3$N were added at −10° C. After 24 hours the reaction solution was concentrated to dryness in vacuo at 40° C. The residue was dissolved in 33% AcOH. The solution was purified by gel filtration on a column of "Sephadex G-15" equilibrated with 33% AcOH. The fraction of the AcOH eluate which was split by treatment with trypsin with liberation of p-nitroaniline was concentrated to dryness in vacuo. The residue was dissolved in 30 ml of MeOH and the solution was added dropwise, while vigorously stirring, to 300 ml of absolute ether.

This resulted in the precipitation of N$^\alpha$-Cbo-Gly-Arg-pNA.HBr. The ethereal phase was sucked off, and the solid phase was washed twice with portions of 100 ml of absolute ether in order to remove the MeOH and traces of AcOH. After drying in vacuo over NaOH platelets there were obtained 4.45 g (78.6% of the theory) of an amorphous powder which was homogeneous in the SS C as shown by TLC.

Elementary analysis and calculation from the empirical formula $C_{22}H_{28}N_7O_6Br$ gave the following values: C=46.33% (46.65%), H=5.04% (4.98%), N=17.88% (17.31%) and Br=14.20% (14.11%).

(Xc) N$^\alpha$-Cbo-C.Cyclohexylglycyl-Gly-Arg-pNA.HCl 2.85 g (5 mmoles) of the compound prepared according to Example 10, paragraph Xb), were deblocked according to Example 10, paragraph Xb), and dissolved in 20 ml of DMF. After cooling to −10° C., 0.70 ml (5 mmoles) of Et$_3$N and then 2.30 g (5.5 mmoles) of N$^\alpha$-Cbo-L-C.cyclohexyl-glycine-p-nitrophenylester (m.p. 93°-94° C.) were added to the solution. The reaction solution was further treated according to Example 10, paragraph (Xb). Purification: gel filtration on "Sephadex G-15" in 33% AcOH. Yield: The fraction of the AcOH eluate which was split by treatment with trypsin with liberation of p-nitroaniline was freeze-dried after the addition of 400 μl (5 mmoles) of conc. HCl. There were obtained 2.47 g (74.7% of the theory) of an amorphous powder which was homogeneous in the SS C as shown by TLC.

Elementary analysis and calculation from the empirical formula $C_{30}H_{41}N_8O_7Cl$ gave the following values: C=54.15% (54.50%), H=6.33% (6.25%), N=17.18% (16.95%) and Cl=5.18% (5.36%).

The amino acid analysis confirmed the presence of the expected amino acids in the correct proportions: Arg: 0.97—Gly: 1.00—L-C.Cyclohexylglycine: 1.05.

EXAMPLE 11

XI. H-L-C.Cyclohexylglycyl-Gly-Arg-pNA.2HCl 660 mg (1 mmole) of N$^\alpha$-Cbo-L-C.cyclohexylglycyl-Gly-Arg-pNA.HCl prepared according to Example 10 were deblocked according to Example 10, paragraph Xb). Purification: gel filtration on "Sephadex G-15" in 33% AcOH. Yield: The fraction of the AcOH eluate which was split by treatment with trypsin with the liberation of p-nitroaniline was freeze-dried after the addition of 160 μl (2 mmoles) of conc. HCl. There were obtained 465 mg (84.9% of the theory) of an amorphous powder which was homogeneous in SS C as shown by TLC.

Elementary analysis and calculation from the empirical formula $C_{22}H_{36}N_8O_4Cl_2$ gave the following values: C=47.95% (48.26%), H=6.75% (6.63%), N=20.90% (20.47%) and Cl=12.42% (12.95%).

The amino acid analysis confirmed the presence of the expected amino acids in the correct proportions: Arg: 0.99—Gly: 1.00—L-C.Cyclohexylglycine: 1.03.

EXAMPLE 12

XII. N$^\alpha$-Bz-L-C.Cyclohexylglycyl-Gly-Arg-pNA.HCl 550 mg (1 mmole) of the compound obtained according to Example 11 were dissolved in 10 ml of DMF. After cooling to −10° C., 140 μl (1 mmole) of Et$_3$N and then 340 mg (1.5 mmoles) of Bz$_2$O were added to the solution. After a few hours the temperature of the reaction solution had reached 20° C. The solution was again cooled to −10° C. and buffered with 140 μl (1 mmole) of Et$_3$N. After 4 hours another 140 μl of Et$_3$ N were added at −10° C. 16 hours later the reaction solution was concentrated to dryness in vacuo at 40° C. The residue was dissolved in 20 ml of MeOH. Gel filtration on a "Sephadex LH-20" column equilibrated with MeOH and elution with MeOH gave 530 mg of a slightly impure product. For a further purification the product was dissolved in 33% AcOH, charged on a "Sephadex G-15" column equilibrated with 33% AcOH and eluted with 33% AcOH. The fraction of the AcOH eluate which was split by treatment with trypsin with liberation of p-nitroaniline was freeze-dried after the addition of 80 μl (1 mmole) of conc. HCl. There were obtained 475 mg (75.3% of the theory) of an amorphous powder which was homogeneous in the SS C as shown by TLC.

Elementary analysis and calculation from the empirical formula $C_{29}H_{39}N_8O_6Cl$ gave the following values: C=54.92% (55.19%), H=6.34% (6.23%), N=17.96% (17.76%) and Cl=5.51% (5.62%).

The amino acid analysis confirmed the presence of the expected amino acids in the correct proportions: Arg: 1.01—Gly: 1.0—L-C-Cyclohexylglycine: 0.98.

EXAMPLE 13

XIII. H-D-C.Cyclohexylglycyl-Gly-Arg-pNA.2HCl (XIIIa)

N$^\alpha$-Cbo-D-C.Cyclohexylglycyl-GLy-Arg-pNA.HCl 2.85 g (5 mmole) of the compound prepared according to Example 10, paragraph (Xb), were deblocked according to Example 10, paragraph (XB), and dissolved in 20 ml of DMF. After cooling to −10° C., 0.70 ml (5 mmoles) of Et$_3$N and then 2.30 g (5.5 mmoles) of N$^\alpha$-Cbo-D-C.cyclohexylglycine-p-nitrophenyl ester. (m.p. 93.5° C.) were added to the solution. The reaction solution was further treated according to Example 10, paragraph (Xb).

Purification: gel filtration on "Sephadex G-15" in 33% AcOH. Yield: The fraction of the AcOH eluate which was split by treatment with trypsin with liberation of p-nitroaniline was freeze-dried after the addition of 400 μl (5 mmoles) of conc. HCl. There were obtained 2.55 g. (77.1% of the theory) of an amorphous powder which was homogeneous in the SS C as shown by TLC.

Elementary analysis and calculation from the empirical formula $C_{30}H_{41}N_8O_7Cl$ gave the following values: C=54.01% (54.50%), H=6.30% (6.25%), N=17.05% (16.95%) and Cl=5.28% (5.36%).

(XIIIb) H-D-C.Cyclohexylglycyl-Gly-Arg-pNA.2HCl 660 mg (1 mmole) of N$^\alpha$-Cbo-D-C.cyclohexylglycyl-Gly-Arg-pNA.HCl prepared according to Example 13, paragraph (XIIIa), were deblocked according to Example 10, paragraph Xb).

Purification: gel filtration on "Sephadex G-15" in 33% AcOH. Yield: The fraction of the AcOH eluate which was split by treatment with trypsin with liberation of p-nitroaniline was freeze-dried after the addition of 160 μl (2 mmoles) of conc. HCl. There were obtained 460 mg (84.0% of the theory) of an amorphous powder which was homogeneous in the SS C as shown by TLC.

Elementary analysis and calculation from the empirical formula $C_{28}H_{36}N_8O_4Cl_2$ gave the following values: C=48.05% (48.26%), H=6.73% (6.63%), N=20.91% (20.47%) and Cl=12.50% (12.95%).

The amino acid analysis confirmed the presence of the expected amino acids in the correct proportions: Arg: 1.01—Gly: 1.00—D-C.Cyclohexylglycine: 0.97.

EXAMPLE 14

XIV. N$^\alpha$-Bz-D-C.Cyclohexylglycol-Gly-Arg-pNA.HCl 550 mg (1 mmole) of the compound prepared according to Example 13 were dissolved in 10 ml of DMF. After cooling to $-10°$ C., 140 μl (1 mmole) of Et$_3$N and then 340 mg (1.5 mmoles) of Bz$_2$O were added to the solution, and the reaction solution was further treated according to Example 12, paragraph (XIIc).

Purification: gel filtration on "Sephadex G-15" in 33% AcOH. Yield: The fraction of the AcOH eluate which was split by treatment with trypsin with liberation of p-nitroaniline was freeze-dried after the addition of 80 μl (1 mmole) of conc. HCl. There were obtained 450 mg (71.3% of the theory) of an amorphous powder which was homogeneous in the SS C as shown by TLC.

Elementary analysis and calculation from the empirical formula C$_{29}$H$_{39}$N$_8$O$_6$Cl gave the following values: C=54.70% (55.19%), H=6.25% (6.23%), N=18.01% (17.76%) and Cl=5.55% (5.62%).

The amino acid analysis confirmed the presence of the expected amino acids in the correct proportions: Arg: 0.96—Gly: 1.00—D-C.Cyclohexylglycine: 0.98.

EXAMPLE 15

XV. N$^\alpha$-Cbo-Val-Gly-Arg-pNA.HCl 2.85 g (5 mmoles) of the compound prepared according to Example 10, paragraph (Xb), were deblocked according to Example 10, paragraph (Xb), and dissolved in 20 ml of DMF. After cooling to $-10°$ C., 0.70 ml (5 mmoles) of Et$_3$N and then 2.05 g (5.5 mmoles) of Cbo-Val-OpNP were added to the solution. The reaction solution was further treated according to Example 10, paragraph (Xb).

Purification: gel filtration on "Sephadex G-15" in 33% AcOH. Yield: The fraction of the AcOH eluate which was split by treatment with trypsin with liberation of p-nitroaniline was freeze-dried after the addition of 400 μl (5 mmoles) of conc. HCl. There were obtained 2.55 g (82.1% of the theory) of an amorphous powder which was homogeneous in the SS C as shown by TLC.

Elementary analysis and calculation from the empirical formula C$_{27}$H$_{37}$N$_8$O$_7$Cl gave the following values: C=52.12% (52.21%), H=6.16% (6.00%), N=18.48% (18.04%) and Cl=5.63% (5.71%).

The amino acid analysis confirmed the presence of the expected amino acids in the correct proportions: Arg: 1.01—Gly: 1.00—Val: 0.97.

EXAMPLE 16

XVI. H-D-Val-Gly-Arg-pNA.2HCl (XVIa) N$^\alpha$-Cbo-D-Val-Gly-Arg-pNA.HCl 2.85 g (5 mmoles) of the compound prepared according to Example 10, paragraph Xb), were deblocked according to Example 10, paragraph Xb), and dissolved in 20 ml of DMF. After cooling to $-10°$ C., 0.70 ml (5 mmoles) of Et$_3$N and then 2.05 1 g (5.5 mmoles) of Cbo-D-Val-OpNP were added to the solution. The reaction solution was further treated according to Example 10, paragraph Xb).

Purification: gel filtration on "Sephadex G-15" in 33% AcOH. Yield: The fraction of the AcOh eluate which was split by treatment with trypsin with liberation of p-nitroaniline was freeze-dried after the addition of 400 μl (5 mmoles) of conc. HCl. There were obtained 2.45 g (78.9% of the theory) of an amorphous powder which was homogeneous in the SS C as shown by TLC.

Elementary analysis and calculation from the empirical formula C$_{27}$H$_{37}$N$_8$O$_7$Cl gave the following values: C=51.95% (52.21%), H=6.10% (6.00%), N=18.33% (18.04%) and Cl=5.60% (5.71%).

XVI. H-D-Val-Gly-Arg-pNA.2HCl 620 mg (1 mmole) of N$^\alpha$-Cbo-D-Val-Gly-Arg-pNA.HCl prepared according to Example 16, paragraph (XVIa), were deblocked according to Example 10, paragraph (Xb).

Purification: gel filtration on "Sephadex G-15" in 33% AcOH. Yield: The fraction of the AcOH eluate which was split by treatment with trypsin with liberation of p-nitroaniline was freeze-dried after the addition of 160 μl (2 mmoles) of conc. HCl. There were obtained 360 mg (68.8% of the theory) of an amorphous powder which was homogeneous in the SS C as shown by TLC.

Elementary analysis and calculation from the empirical formula C$_{19}$H$_{32}$N$_8$O$_5$Cl$_2$ gave the following values: C=42.98% (43.60%), H=6.24% (6.16%), N=21.88% (21.41%) and Cl=13.12% (13.55%).

The amino acid analysis confirmed the presence of the expected amino acids in the correct proportions: Arg: 0.96—Gly: 1.00—D-Val:0.98.

The substrates according to the invention, e.g. the substrate prepared according to Example 1, viz. N$^\alpha$-Bz-Val-Gly-Arg-pNA.HCl, were used for the quantitative determination of various enzymes in blood plasma. The determination was carried out by taking advantage of the fact that the split product (NH$_2$-R$^2$) formed by enzymatic hydrolysis of the substrate has an UV spectrum which differs from that of the substrate and is shifted toward higher wave lengths. Thus, the substrate according to Example 1, i.e. N$^\alpha$-Bz-Val-Gly-Arg-pNA.HCl, has an absorption maximum at 302 nm (nanometer) and a molar extinction coefficient of 12,950. The absorption of the substrate is practically nil at 405 nm. p-Nitroaniline, the split product (NH$_2$-R$^2$) formed by the enzymatic hydrolysis of the substrate has an absorption maximum at 380 nm and a molar extinction coefficient of 13,200. At 405 nm the extinction coefficient is but moderately reduced, i.e. to 9,650.

The degree of the enzymatic hydrolysis of the substrate, which is proportional to the quantity of p-nitroaniline formed, can be easily determined by spectrophotometric measurement at 405 nm. The presence of an excess of substrate thus does not disturb the measurement at 405 nm. The conditions are practically the same for the other subtrates of the invention carrying a p-nitroanilino group as the chromophoric group. The spectrophotometric measurement was, therefore, carried out in all cases at 405 nm.

The enzymatic hydrolysis reaction can be represented by the following scheme:

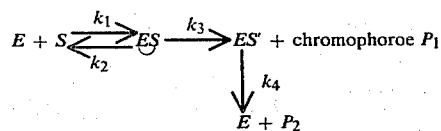

E = enzyme
S = substrate

ES = enzyme-substrate complex
P$_1$ and P$_2$ = products
k$_1$, k$_2$, k$_3$ and k$_4$ = rate constants
Dissociation constant for ES = k$_2$/k$_1$ = K$_m$ (Michaelis constant)
If [S] >> [E] and k$_4$ << k$_3$, the following is true:

$$K_m = \frac{([E] - [ES]) \cdot [S]}{[ES]} \quad (1)$$

The rate constant at which chromophore P$_1$ is formed is $$v = k_3 \cdot [ES]$$

$$v = \frac{k_3 \cdot [E] \cdot [S]}{K_m + [S]} \quad (2)$$

If E is completely bound to S, then [ES] = [E] and $$v = v_{max} = k_3 \cdot [E] \quad (3)$$

Lineweaver-Burk equation:

$$\frac{1}{v} = \frac{K_m}{v_{max}} \cdot \frac{1}{[S]} + \frac{1}{v_{max}} \quad (4)$$

As is evident from equation (2) constants K$_m$ and k$_3$ determine the activity of the substrate for a given enzyme. For determining these constants the following procedure is followed:

The enzyme and the substrate are mixed in a buffer solution, and the hydrolysis reaction is followed for 2 to 30 minutes. The concentration of substrate [S] is varied, whereas the enzyme concentration is kept constant. If the extinction (OD = optical density) is plotted in a co-ordinate system as a function of time, a curve is obtained the tangent of which at time zero corresponds to the ideal course of the hydrolysis. By means of this tangent the initial rate of the hydrolysis can be determined.

If 1/v is plotted against 1/[S], a Lineweaver-Burk diagram (cf. "Kurzes Lehrbuch der Biochemie" by P. KARLSON, Georg Thieme-Verlag, Stuttgart, 1967, p. 70) is obtained from which v$_{max}$ and K$_m$ can be determined graphically.

K$_m$ and k$_3$ = v$_{max}$/E were determined with the substrates of the invention, e.g. N$^\alpha$-Bz-Val-Gly-Arg-pNA.HCl (substrate according to Example 1) for urokinase. The results are summarized in Table I.

TABLE I

| Urokinase activity, determined by means of a substrate according to the invention | | |
|---|---|---|
| Substrate | K$_m$ mole/liter | v$_{max}$ μmole/min. |
| I | 6.06 × 10$^{-5}$ | 7.27 × 10$^{-5}$ CTA |

| Trypsin activity, determined by means of a substrate according to the invention | | |
|---|---|---|
| XVI | 1.83 × 10$^{-5}$ | 4.17 × 10$^{-3}$ NF |

The values of K$_m$ and v$_{max}$ established for urokinase and trypsin with the other substrates of the invention are of the same order of magnitude, which indicates that the said substrates have a particularly high susceptibility to urokinase and trypsin.

For the determination of the kinetic constants K$_m$ and v$_{max}$ listed in Table I aqueous dilution series of the substrates with concentrations from 0.1 to 2 μmoles/ml were used. A measuring vessel was charged with 2 ml of TRIS-imidazole buffer having a pH of 8.4, an ionic strength of 0.30 and a temperature of 37° C., and then 0.25 ml of an aqueous urokinase solution having a concentration of 400 CTA/ml was added to the buffer solution. The mixture was pre-incubated for 1 minute at 37° C. Thereafter, 0.25 ml of substrate solution was added to the pre-incubated mixture. The course of the enzymatic hydrolysis of the substrate at the various substrate concentrations was followed by means of a photometer at 405 nm for 10 minutes. The value of the quantity of p-nitroaniline formed per minute is a measure for the rate of hydrolysis at a given substrate concentration. In a coordinate system the reciprocal values of the substrate concentrations were plotted on the abscissa and the corresponding reciprocal values of the rate of hydrolysis were plotted on the ordinate. In the so-called Lineweaver-Burk diagram a straight curve was obtained for the substrates listed in Table I, which proves that the hydrolysis of the substrates caused by urokinase follows the law of Michaelis-Menten and that, therefore, the substrates are ideal for the determination of urokinase. The kinetic constants K$_m$ and v$_{max}$ were determined from the points of intersection of the curves with the abscissa and the ordinate.

TABLE II

| 1 μmole of pNA per minute from substrate I | corresponding other units |
|---|---|
| urokinase | 20250 CTA |
| urine kallikrein | 1688 BAEE |
| human thrombin | 2174 NIH |
| human plasmin | 6850 CU |
| bovine trypsin | 36.6 NF |

BAEE (Benzoyl-L-arginine ethyl ester)—1 BAEE unit of urine kallikrein is that quantity of enzyme which hydrolyzes 1 μmole of benzoyl-L-arginine ethyl ester per minute under standard conditions.

NIH is a unit which was standardized by the "US National Institute of Health".

CU is the casein unit which is measured on casein under standard conditions.

NF is the trypsin unit, i.e. that quantity of enzyme which casues a change in the absorption Δ OD of 0.003 per minute, measured on benzoyl-L-arginine ethyl ester under standard conditions (cf. "The National Formulary XII", edited by "The American Pharmaceutical Association", Washington, D.C., 1965, pages 417–418).

In the first column of Table II are listed the quantities of the various enzymes which split substrate I at a temperature of 37° C., a pH of 8.4, an ionic strength of 0.3 and a substrate concentration of 10$^{-4}$ mole with a velocity of 1 μmole per minute. In the second column the corresponding enzyme quantity, expressed in other enzyme unities, is indicated. From Table II it can be seen that the enzyme kallikrein present in urine together with urokinase is split but little by substrate I and that, consequently, kallikrein does not disturb the determination of urokinase in urine. Also, thrombin is split very little and unspecifically by substrate I.

TABLE III

Urokinase activity, measured by means of the substrates of the invention at constant substrate and urokinase concentrations, 37° C., a pH of 8.4 and an ionic strength of 0.3

| Substrate | Quantity in nanomoles of the split product $NH_2$-$R^2$ produced by 100 CTA units of urokinase in 1 minute |
|---|---|
| I | 3.64 pNA |
| II | 0.92 pNA |
| III | 3.21 pNA |
| IV | 1.00 pNA |
| V | 2.82 pNA |
| VI | 2.91 pNA |
| VII | 1.73 pNA |
| VIII | 1.32 pNA |
| IX | 1.13 pNA |
| X | 1.50 pNA |
| XI | 1.33 pNA |
| XII | 3.56 pNA |
| XIII | 1.78 pNA |
| XIV | 1.05 pNA |
| XV | 1.12 pNA |
| XVI | 0.20 pNA |

In the appended drawing the sole FIGURE represents a graph in which the change in the optical density Δ OD caused by the hydrolytic action of various quantities of urokinase on substrate I within 10 minutes is plotted as a function of the urokinase quantity in a coordinate system. From this graph it can be seen that urokinase concentrations can be determined accurately in the range of 1 to 10 CTA/ml. In the determination of the urokinase content in the urine of 14 healthy test persons values of about 8 CTA units per ml of urine were found.

The determination of urokinase in urine is particularly important since it permits, as already mentioned, the detection of pathological conditions in a relatively simple and rapid manner. The method which has been most used up to now for the determination of urokinase in urine is the so-called fibrin plate method [I. BJERREHUUS, Scand. J. Clin. Lab. Invest. 4, 179 (1952)]; [F. E. SMYRNIOTIS et al., Thromb. Diath. et Haemorrh. vol. III, 258 (1959)] which is carried out as follows: Fibrin plates (fibrinogen content: 0.2%) are prepared according to the method of MULLERTZ [Acta physiol. Scand. 26, 174 (1954)]. For each urokinase determination one fibrin plate and 30 lambda drops (lambda drop pipette) of urine, undiluted, diluted 1:2 and diluted 1:4, respectively, are used (if the urokinase concentration is too high, the dilution factors can be doubled). The plates are incubated for 16 hours at 30° C. The lyzed zones are made visible by the addition of a drop of Congo red (0.1%). The product of two diameters (of the lyzed zones) positioned at right angles is used as a measure of the lyzed zones. The urokinase concentration (units per ml) is determined by means of a reference curve which is established by using a dilution series with standard urokinase.

In this method the urokinase concentration is not determined directly but via the quantity of plasmin produced from plasminogen by the action of urokinase. Based on the determination of end products resulting from a chain of reactions, this method is subject to various sources of error. Further serious disadvantages result from the fact that the incubation time is very long and that a reference curve has to be established for each determination. Furthermore, the valuation of the results is relatively complex and inaccurate because the reference curve is not linear.

By using the substrates of this invention the disadvantages of the above described method of determination can be entirely overcome since the measurement of the urokinase concentration is effected directly and the measuring results are not distorted by side reactions. Furthermore, the measuring results are available already after 10 minutes, an advantage which is particularly important for clinical diagnosing. A further advantage resides in the fact that the measuring results can be expressed in substrate units. A change in the optical density Δ OD of 0.010/minute corresponds to a concentration of 1 milli-unit of urokinase per ml of the test sample.

When plasminogen activators have to be determined in blood plasma, it is often advantageous to carry out the determination in a buffer solution containing aprotinin and/or hirudin since the latter do not inhibit the plasminogen activators but exert an inhibiting action on other activated plasma enzymes, such as thrombin, plasmin and plasma kallikrein, which may be present and, under certain circumstances, may have a disturbing effect on the determination of plasminogen activators. For instance, a TRIS-imidazole or glycine buffer having a pH of 8.2 to 8.6 and an ionic strength of 0.15 and 1.0, and to which 0.02 to 0.2 trypsin-inhibiting units of aprotinin and/or 0.001 to 10 antithrombin units of hirudin per ml have been added, can be used.

When the determination of urokinase has to be carried out with body fluids or tissue extracts containing inhibitors of urokinase, it may be advantageous to add an excess of urokinase, to incubate the mixture for a few minutes and then to determine the remaining urokinase activity by adding the substrate and measuring the quantity of the split product.

Furthermore, it was surprisingly observed that the substrates of the invention, due to their particular conformation, are also very sensitive to trypsin and that the latter is catalytically split at unexpectedly high velocities. The new substrates are particularly well suited for the determination of trypsin in duodenal juice and in the blood of patients suffering from acute pancreatitis where trypsin gets into the blood stream but, due to the high blood volume, is present at a low concentration only. The known substrates which have been used up to now for the determination of trypsin have a sensitivity which is much too low for determining such low trypsin concentrations.

The determination of trypsin in duodenal juice can be carried out for instance as follows: 1.79 ml of trisimidazole buffer having a pH of 8.4 and an ionic strength of 0.30 are mixed with 0.01 ml of duodenal juice at 37° C. in a measuring vessel. Thereafter, the mixture is rapidly mixed with 0.2 ml of a $2 \times 10^{-3}$ molar solution of a substrate of this invention. The quantity of p-nitroaniline released from the substrate by the action of trypsin is determined by measuring the change in the optical density Δ OD per minute at a wave length of 405 nm. The quantity of p-nitroaniline released per minute of the corresponding change in the optical density is proportional to the trypsin activity. When using the substrate prepared according to Example 10, i.e. $N^\alpha$-Cbo-C.cyclohexylglycyl-Gly-Arg-pNA.HCl, trypsin can be determined for instance at concentrations as low as 0.01 NF unit per ml of test sample.

The following Table IV comprises the values of the activity of bovine trypsin, measured by means of the substrates of the invention at constant substrate and enzyme concentrations.

TABLE IV

Activity of bovine trypsin, measured by means of the substrates of the invention at constant substrate and enzyme concentrations. For comparison, the corresponding values determined with $N^\alpha$-Bz-Phe-Val-Arg-pNA . HCl and $N^\alpha$-Bz-DL-Arg-pNA . HCl are listed.

| Substrate concentration $2 \times 10^{-4}$ M | Quantity in nanomoles of p-nitroaniline enzymatically released from the substrate by 1 NF unit of trypsin in 1 minute |
|---|---|
| $N^\alpha$-Bz-Phe-Val-Arg-pNA . HCl | 8,4 |
| $N^\alpha$-Bz-DL-Arg-pNA . HCl | 0,45 |
| I | 20,9 |
| II | 10,8 |
| III | 28.5 |
| IV | 19.2 |
| V | 15.9 |
| VI | 19.1 |
| VII | 25.7 |
| VIII | 14.2 |
| IX | 17.5 |
| X | 46.7 |
| XI | 20.0 |
| XII | 37.9 |
| XIII | 28.8 |
| XIV | 41.9 |
| XV | 41.3 |
| XVI | 33.3 |

The results listed in Table IV were obtained under the following experimental conditions: In a measuring vessel 1.7 ml of tris-imidazole buffer having a pH of 8.4 and an ionic strength of 0.30 were mixed at 37° C. with 0.1 ml of an aqueous trypsin solution having a concentration of 2 NF units of trypsin per ml. To the mixture 0.2 ml of a $2 \times 10^{-3}$ molar solution of the substrate to be tested was added. Thereafter, the quantity of p-nitroaniline released from the substrate by the action of the trypsin was determined by measuring the change in the optical density $\Delta$ OD per minute at a wave length of 405 nm.

The substrates of the invention can also be used for the determination of inhibitors of the plasminogen activators, e.g. urokinase inhibitors. This determination can be carried out by incubating a predetermined quantity of urokinase with a body fluid containing urokinase inhibitors in the presence or absence of a buffer system, diluting the incubating mixture with tris-imidazole buffer to a volume of 1.8 ml and adding to the diluted mixture 0.2 ml of a $2 \times 10^{-3}$ molar solution of a substrate according to the invention. The non-inhibited urokinase activity is determined by measuring the charge in the optical density per minute. The difference from the starting urokinase quantity and the remaining urokinase activity is a measure of the quantity of inhibitor initially present in the body fluid. The same method can be used for the determination of trypsin inhibitors.

In the determination of plasminogen preactivators in plasma the said preactivators are first quantitatively activated whereupon the plasminogen activators thus formed are determined by means of the substrates of the invention. The activation of the plasminogen preactivators is effected by incubating the plasma after addition thereto of an active Hagemann factor preparation and adding to the incubate a tris-imidazole buffer containing aprotinin in order to inhibit other enzymes, in particular plasma kallikrein and plasmin, which also form during the activation of the plasminogen preactivators.

For determining trypsinogen in body fluids an activator, e.g. chemotrypsin, is added to the said fluids in order to convert trypsinogen into trypsin which can then be determined by means of a substrate according to the invention in the manner described above.

The principle of the above described determination with the substrates of the invention consists in determining an enzyme, i.e. a plasminogen activator (such as urokinase) or trypsin, which is either already present or has been formed by activation or is still present after inhibition.

I claim:

1. A substrate for use as a reagent in the determination of plasminogen activators, inhibitors thereof and plasminogen preactivators, and trypsin, trypsin inhibitors and trypsinogen in human and mammal body fluids and tissue extracts which has the following structure:

$$R^1—X—Y—Z—NH—R^2 \qquad I$$

wherein X represents a group having the formula $$—NH—CH—CO—$$
$$\qquad | $$
$$\qquad R_3$$

in which $R^3$ is a straight or branched alkyl radical having 1 to 7 carbon atoms or a cyclohexyl or cyclohexylmethyl radical, Y represents a seryl group or a glycol group. Z represents an arginyl group, $R^1$ represents hydrogen or an acyl or sulfonyl group and $R^2$ represents an aromatic hydrocarbon radical optionally carrying substituents which permit chromophoric or fluorescent activity, —NH—$R^2$ being a chromophoric or fluorescent group, and which has the property to release a split product of formula $NH_2R^2$ under the action of plasminogen activators, the quantity of said split product being quantitatively measurable by photometric, spectrophotometric or fluorescence-photometric methods.

2. The substrate according to claim 1 which is protonized with a mineral acid such as HCl, HBr, $H_2SO_4$ or $H_3PO_4$, or an organic acid such as formic, acetic, oxalic or tartaric acid.

3. The substrate according to claim 1 in which the acyl group $R^1$ has the partial formula $R^3$—CO— wherein $R^3$ represents
(a) an aliphatic hydrocarbon radical which has 1 to 17 carbon atoms and which optionally carries an amino group in the $\omega$-position,
(b) an araliphatic hydrocarbon radical whose aliphatic radical has 1 to 17 carbon atoms and which optionally carries an amino group on the aryl radical,
(c) a cycloaliphatic hydrocarbon radical which optionally carries an amino or aminomethyl group,
(d) an aromatic hydrocarbon radical which optionally carries an alkyl, amino or aminoalkyl group, or
(e) a benzyloxy group.

4. The substrate according to claim 1 in which the sulfonyl group $R^1$ is an alkanesulfonyl group the alkane radical of which has 1 to 17 carbon atoms, such as a methane- or ethanesulfonyl group, or an arylsulfonyl group optionally carrying one or more lower alkyl substituents, such as a benzene-, p-toluene- or naphthalene-sulfonyl group.

5. The substrate according to claim 1 in which $R^2$ is a p-nitrophenyl, 2-naphthyl or 4-methyl-2-naphthyl group.

* * * * *

UNITED STATES PATENT AND TRADEMARK OFFICE
CERTIFICATE OF CORRECTION

PATENT NO. : 4,190,574
DATED : February 26, 1980
INVENTOR(S) : Lars G. Svendsen

It is certified that error appears in the above-identified patent and that said Letters Patent are hereby corrected as shown below:

Column 1, line 58, reads "activator is not" should read --activator activity is not--

Column 7, line 22, reads "stirrer", should read --stirring--

Column 19, line 62, reads "2.051g" should read --2.05 g--

Column 24, line 24, reads "0.15 and", should read --0.15 to--

Column 24, line 58 reads "per minute of" should read --per minute or--

Column 26, line 23, reads "R3" should read --$R^3$--

Signed and Sealed this

Fifteenth Day of July 1980

[SEAL]

Attest:

SIDNEY A. DIAMOND

Attesting Officer

Commissioner of Patents and Trademarks